(12) United States Patent
Goddard

(10) Patent No.: US 9,861,463 B2
(45) Date of Patent: Jan. 9, 2018

(54) IMPLANTS AND METHODS OF IMPLANTING THE SAME

(71) Applicant: Boston Scientific Scimed, Inc., Maple Grove, MN (US)

(72) Inventor: James Goddard, Pepperell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 15/216,929

(22) Filed: Jul. 22, 2016

(65) Prior Publication Data

US 2016/0324620 A1    Nov. 10, 2016

Related U.S. Application Data

(63) Continuation of application No. 13/181,952, filed on Jul. 13, 2011, now Pat. No. 9,421,076.

(60) Provisional application No. 61/368,778, filed on Jul. 29, 2010.

(51) Int. Cl.
| | |
|---|---|
| A61F 2/04 | (2013.01) |
| A61F 2/00 | (2006.01) |
| A61B 17/06 | (2006.01) |
| A61B 17/00 | (2006.01) |

(52) U.S. Cl.
CPC ...... *A61F 2/0063* (2013.01); *A61B 17/06166* (2013.01); *A61F 2/0045* (2013.01); *A61B 2017/00805* (2013.01)

(58) Field of Classification Search
CPC .... A61F 2/0036; A61F 2/0045; A61F 2/0063; A61F 2002/0072; A61B 2017/00805
See application file for complete search history.

(56) References Cited

U.S. PATENT DOCUMENTS

| 6,010,447 A | 1/2000 | Kardjian |
| 2002/0082619 A1 | 6/2002 | Cabak et al. |
| 2004/0144395 A1 | 7/2004 | Evans et al. |
| 2007/0032695 A1 | 2/2007 | Weiser |
| 2009/0171142 A1 | 7/2009 | Chu |

(Continued)

FOREIGN PATENT DOCUMENTS

| WO | 2006/046950 A1 | 5/2006 |
| WO | 2012/015619 A1 | 2/2012 |

OTHER PUBLICATIONS

International Search Report and Written Opinion for International Application No. PCT/US2011/44360, dated Sep. 15, 2011, 15 pages.

(Continued)

*Primary Examiner* — Charles A Marmor, II
*Assistant Examiner* — Thaddeus Cox
(74) *Attorney, Agent, or Firm* — Brake Hughes Bellermann LLP

(57) ABSTRACT

In one embodiment, an apparatus includes a support member and a suture. The support member is configured to provide support to a portion of a body of a patient. The support member has a first end portion and a second end portion. The first end portion of the support member is configured to be disposed within a body of a patient. The suture is removably coupled to the first end portion of the support member and is configured to extend through an incision in the body of the patient from a location within the body of the patient to a location outside of the body of the patient.

12 Claims, 5 Drawing Sheets

(56) References Cited

U.S. PATENT DOCUMENTS

| | | |
|---|---|---|
| 2009/0221868 A1 | 9/2009 | Evans |
| 2009/0259094 A1* | 10/2009 | Bouchier .............. A61F 2/0045 600/37 |
| 2010/0094079 A1 | 4/2010 | Inman et al. |
| 2011/0124954 A1 | 5/2011 | Ogdahl et al. |
| 2012/0029274 A1 | 2/2012 | Goddard |

OTHER PUBLICATIONS

Non-final Office Action for U.S. Appl. No. 13/181,952, dated Mar. 6, 2013, 13 pages.
Response to Non-Final Office Action for U.S. Appl. No. 13/181,952, filed Jun. 6, 2013, 7 pages.
Final Office Action for U.S. Appl. No. 13/181,952, dated Sep. 13, 2013, 14 pages.
Response to Final Office Action for U.S. Appl. No. 13/181,952, dated Nov. 26, 2013, 8 pages.
Non-Final Office Action for U.S. Appl. No. 13/181,952, dated Feb. 12, 2014, 15 pages.
Response to Non-Final Office Action for U.S. Appl. No. 13/181,952, filed Apr. 29, 2014, 8 pages.
Final Office Action for U.S. Appl. No. 13/181,952, dated Sep. 11, 2014, 17 pages.
Response to Final Office Action for U.S. Appl. No. 13/181,952, filed Dec. 10, 2014, 8 pages.
Non Final Office Action for U.S. Appl. No. 13/181,952, dated Jul. 16, 2015, 12 pages.
Response to Non-Final Office Action for U.S. Appl. No. 13/181,952, filed Oct. 14, 2015, 8 pages.
Notice of Allowance for U.S Appl. No. 13/181,952, dated Oct. 30, 2015, 5 pages.
Office Action for EP Patent Application No. 11735757.4, dated Dec. 23, 2015, 5 pages.
U.S. Appl. No. 13/181,952, filed Jul. 13, 2011.

* cited by examiner

IMPLANTS AND METHODS OF IMPLANTING THE SAME

CROSS-REFERENCE TO RELATED APPLICATIONS

This application is a continuation of, and claims priority to, U.S. patent application Ser. No. 13/181,952, filed on Jul. 13, 2011, now U.S. Pat. No. 9,421,076, entitled "IMPLANTS AND METHODS OF IMPLANTING THE SAME", which, in turn, claims priority to U.S. Provisional Patent Application No. 61/368,778, filed Jul. 29, 2010, entitled "IMPLANTS AND METHODS OF IMPLANTING THE SAME", the disclosures of which are incorporated by reference herein in their entirety.

TECHNICAL FIELD

This disclosure relates generally to medical devices and more particularly to implants configured to provide support within a pelvic region of a patient.

BACKGROUND

A variety of medical procedures are performed to treat various female pelvic dysfunctions, including procedures to treat urinary incontinence, and correcting various prolapse conditions such as uterine prolapse, cystoceles, rectoceles, and vaginal vault prolapse.

Known implants are configured to provide support to a patient's body to treat stress urinary incontinence. Some known implants require that a single bodily incision be made and are positioned or tensioned by controlling how far into the tissue the end portions are deposited or pushed into the anchoring tissue. Such known implants, however, can be difficult to correctly place and tension within the body of the patient.

Some known implants require that entrance and exit incisions be used to place the implant within the body of the patient. Such implants make use of sutures that are bio-resorbable so that the sutures will not be a long term irritant to the body of the patient. Such bio-resorbable sutures, however, can be expensive and time consuming to manufacture and package.

Thus, it would be desirable to provide an implant that facilitates the positioning and tensioning within the body of the patient and does not require the use of bio-resorbable sutures.

SUMMARY

In one embodiment, an apparatus includes a support member and a suture. The support member is configured to provide support to a portion of a body of a patient. The support member has a first end portion and a second end portion. The first end portion of the support member is configured to be disposed within a body of a patient. The suture is removably coupled to the first end portion of the support member and is configured to extend through an incision in the body of the patient from a location within the body of the patient to a location outside of the body of the patient.

DETAILED DESCRIPTION

The devices and methods described herein are generally directed to implants and the delivery and placement of such implants within a pelvic region (also referred to herein as "pelvis") of a patient. The devices and implants described herein may be used with a female patient as well as a male patient.

Various embodiments of implants are described herein. An implant can be delivered to a pelvic region of a patient using a variety of different delivery devices, only some examples of which are described herein.

As used herein, the terms proximal portion or proximal end refer to the portion or end, respectively, of a device that is closest to a physician when performing a medical procedure, and the terms distal portion or distal end refer to the portion or end, respectively, of the device that is furthest from the physician during a medical procedure. For example, a distal end or portion of a sleeve assembly or dilator device as described herein refers to the end or portion of the device that is first inserted into a body of a patient during a medical procedure. The proximal end or portion is the end or portion of the device that is inserted into a body of the patient after the distal end or distal portion. The terms "trailing end" and "leading end" are also referred to herein and have similar meanings as proximal and distal, respectively. As used herein, the term "leading end" refers to the end of a device or apparatus that is inserted into a body first. The term "trailing end" refers to the end of the device or apparatus that is inserted into the body after the leading end.

Figure 1:
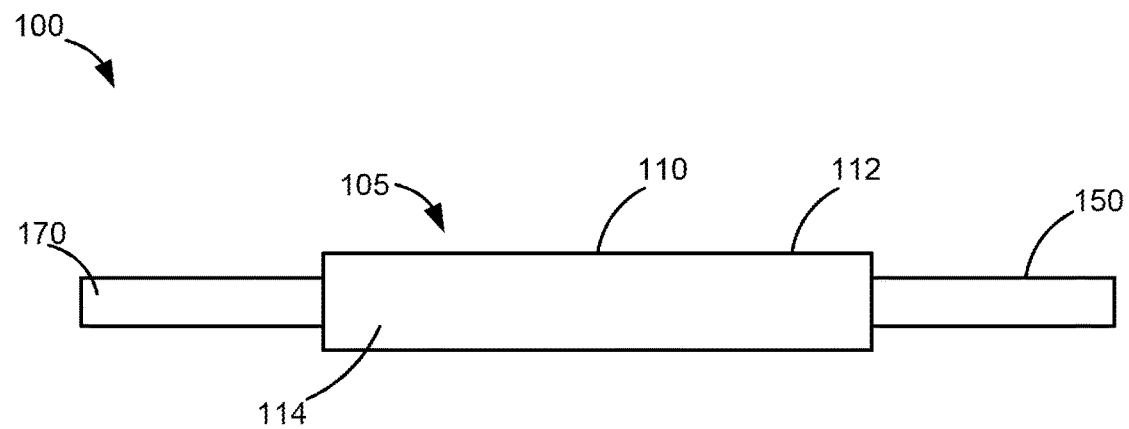
FIG. 1 is a schematic illustration of an apparatus according to an embodiment of the invention.

FIG. 1 is a schematic illustration of an apparatus 100 according to an embodiment. The apparatus 100 includes an implant 105, a first suture 150, and a second suture 170. The implant 105 has a support member 110, a first end portion 112, and a second end portion 114.

The implant 105 is configured to be disposed in a body of a patient. The support member 110 is configured to provide support to a portion of the body of the patient. For example, in some embodiments, the support member 110 is configured to be placed or disposed adjacent a bladder or a bladder neck of a patient and to provide support to the bladder or bladder neck of the patient. Although many of the procedures described herein are focused on placing the implant within a body of a female patient, it should be understood that the devices and methods described herein may be used in connection with a male patient.

The first end portion 112 and the second end portion 114 are configured to be disposed within bodily tissue of the patient. In some embodiments, the first end portion 112 and the second end portion 114 are configured to be coupled to such bodily tissue to help secure the implant 105 in place within the body of the patient.

The first end portion 112 and the second end portion 114 can be of any shape or size suitable for extending between the support member 110 and the bodily tissue and coupling to the bodily tissue. Additionally, the implant 105 may include additional arm members or end portions that are configured to couple to bodily tissue to help secure the implant 105 in place within the body of the patient.

In some embodiments, the first end portion 112 and the second end portion 114 are configured to be disposed within and coupled to an obturator membrane of the patient or other pelvic tissue of the patient. In other embodiments, the first end portion 112 and the second end portion 114 are configured to be coupled to other bodily tissue.

In some embodiments, the first end portion 112 and the second end portion 114 include tangs or tanged portions configured to help anchor the end portions 112 and 114 within the bodily tissue of the patient. The terms "tanged" or "tangs" as used herein mean roughened or jagged edges or areas, such as can result from cutting a woven or knit mesh material. In other embodiments, the end portions 112 and 114 include barbs, dimples and/or other protrusions configured to engage the bodily tissue of the patient to help retain the implant 105 in place within the body of the patient. In other embodiments, other mechanisms may be used to couple the end portions 112 and 114 to the bodily tissue.

The implant 105 can be formed with a mesh material to allow tissue in-growth to the implant 105 after implantation within the body of the patient. For example, some or all of the implant 105 can be formed with a mesh material as described in U.S. Patent Pub. 2005/0038452 A1 to Chu, the entirety of which is hereby incorporated by reference. In some embodiments, some or all of an implant 105 can be formed with the Advantage™ Mesh or the Polyform™ Synthetic Mesh material each provided by Boston Scientific Corporation.

The implant 105 can be monolithically formed or alternatively, the implant 105 can be formed with multiple different materials and/or can include multiple different components or portions coupled together. In some embodiments, the implant can be formed with a combination of materials including synthetic and biological materials. For example, the support member 110 can be formed with a first biocompatible material and the end portions 112 and 114 can be formed with a second biocompatible material different than the first material. In other embodiments, the support member 110 is formed with a biological material, and the end portions 112 and 114 are formed with a synthetic material. In some embodiments, the end portions 112 and 114 and the support member 110 have a different weave, pitch, texture, color, and pattern from each other.

In some embodiments, the end portions 112 and 114 are formed monolithically with the support member 110. In other embodiments, the end portions 112 and 114 are formed separate from the support member 110 and can be coupled to the support member 110. In such embodiments, the end portions 112 and 114 and the support member 110 can be coupled in an abutting relationship, an overlapping relationship, or can be bridged. The end portions 112 and 114 can be coupled to the support member 110 by, for example, heat bonding, gluing, using fasteners, and/or sewing. In some embodiments, an arm member can include a heat seal along its length or a portion of its length to help prevent or reduce stretching of the arm member.

The first suture 150 is coupled to the first end portion 112 of the support member 110. In some embodiments, the first suture 150 is removably coupled to first end portion 112 of the support member 110. In some embodiments, the entire first suture 150 may be removed from the first end portion 112 of the support member 110 without damaging the first end portions 112.

The first suture 150 may be coupled to the first end portion 112 of the support member 110 using any number of techniques. For example, in one embodiment, the first suture 150 threaded through an opening defined by the first end portion 112 and forms a loop to couple the first suture 150 to the first end portion 112. In such embodiments, the first suture 150 is slidably coupled to the first end portion 112 and may be removed from the first end portion 112 of the support member 110 by severing or cutting one portion of the loop and pulling the first suture 150 in a direction away from the first end portion 112. In other embodiments, the first suture 150 is removably coupled to the first end portion 112 via connector, an adhesive, or another mechanism.

The second suture 170 may be coupled to the second end portion 114 of the support member 110 using the same types of techniques as described with respect to the first suture 150 and the first end portion 112.

In some embodiments, the first suture 150 and the second suture 170 are formed of a non-resorbable material. For example, in some embodiments, the first suture 150 and the second suture 170 are formed of a permanent suture material, such as polypropylene.

In some embodiments, the first suture 150 and the second suture 170 are configured to be inserted into the body of a patient along with the support member 110. The first suture 150 and second suture 170 are configured to extend from the end portions 112 and 114 of the implant 105 located at location within the body of the patient to a location outside of the body of the patient. In some embodiments, the first suture 150 and the second suture 170 each extend through a bodily incision from a location within the body of the patient to a location outside of the body of the patient. In some embodiments, as will be described in more detail below, once the first suture 150 and the second suture 170 each extend from a location within the body of the patient to a location outside of the body of the patient, the first suture 150 and the second suture 170 may be removed from the end portions 112 and 114 of the implant 110 to leave the end portions 112 and 114 disposed within the body of the patient.

For example, in one embodiment, the first suture 150 includes a loop and is threaded through and slideably coupled to end portion 112. Similarly, the second suture 170 includes a loop and is threaded through and slideably coupled to end portion 114. Once the implant 105 is placed such that the end portions 112 and 114 are disposed within the body of the patient and the sutures 150 and 170 extend from the respective end portion through a skin incision to a location outside of the body of the patient, the sutures 150 and 170 may be used to appropriately position and tension the implant 105. A portion of each of the loops of the sutures 150 and 170 may be severed or cut and the sutures 150 and 170 may be pulled in a direction away from the body of the patient. The sutures 150 and 170 will then be pulled through the skin incisions and will be separated from the end portions 112 and 114. Accordingly, the end portions 112 and 114 will be left disposed within the body of the patient.

The implant 105 may be placed within the body of a patient using a number of different methods. In some embodiments, the implant 105 may be placed within the body of the patient by making a single vaginal incision and two exit incisions. The implant 105 may be placed using an inside-out procedure (i.e., passing the implant 105 through a vaginal incision and pushing or pulling the implant 105 to a location within the body of the patient) or an outside-in procedure (i.e., passing an insertion tool through a skin incision and then through a vaginal incision and pulling the implant 105 to a location within the body of the patient).

For example, in one embodiment, the implant 105 is placed or implanted within the body of a patient by making an incision in an anterior wall of the vagina of the patient. End portion 112 is then coupled to an insertion tool. Any number of types of insertion tools may be used. For example, an Obtryx® device as sold by Boston Scientific Corporation may be used. In other embodiments, other insertion tools are used. For example, an insertion tool with a "t" shaped slot configured to receive the suture 150 may be used. In one embodiment, the insertion tool is coupled to the suture 150 and the end portion 112 of the implant 105 is passed through the vaginal incision to a location within the body of the patient. The insertion tool then passes through a skin incision, thereby passing the suture 150 through the skin incision. The insertion tool may then be removed from the suture 150 and associated with suture 170. The end portion 114 may then be passed through the vaginal incision and the end portion 114 may be pushed or pulled to a location within the body of the patient. The insertion tool may then be passed through a second skin incision, thereby passing the suture 170 through the second skin incision. The insertion tool may then be removed from the suture 170.

The sutures 150 and 170 may then be moved (for example, by pulling on the sutures in directions away from the skin incisions) to appropriately place and tension the support member 110 within the body of the patient. For example, in one embodiment, the support member 110 is placed and tensioned below a portion of the bladder of the patient. In other embodiments, the support member 110 is disposed at a different location within the body of the patient. In some embodiments, the sutures 150 and 170 may remain coupled to the end portions 112 and 114 for a few days after the procedure to allow for further adjusting and tensioning of the implant 105.

Once the support member is appropriately placed and tensioned, the sutures 150 and 170 may be removed from the end portions 112 and 114 of the implant 105. In some embodiments, the sutures 150 and 170 may be removed from the end portions 112 and 114 by cutting a portion of the sutures 150 and 170 that is disposed outside of the body of the patient and pulling the sutures 150 and 170 in directions away from the body of the patient.

Figure 2A:
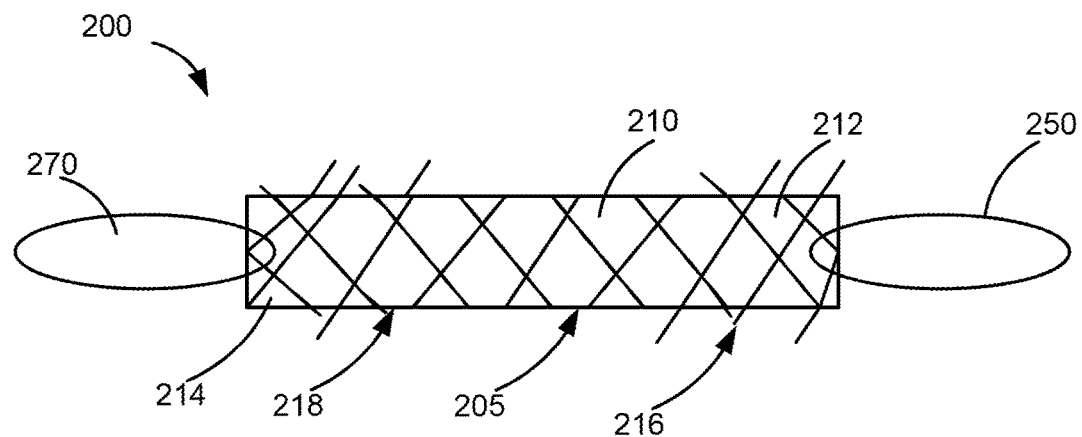
FIG. 2A is a top view of an apparatus according to an embodiment of the invention.

FIG. 2A is a top view of an apparatus 200 according to an embodiment. The apparatus 200 includes an implant 205, a first suture 250, and a second suture 270. The implant 205 includes a support member 210, a first end portion 212, and a second end portion 214.

The implant 205 is configured to be disposed in a body of a patient. The support member 210 is configured to provide support to a portion of the body of the patient. For example, in some embodiments, the support member 210 is configured to be placed or disposed adjacent a bladder or a bladder neck of a patient and to provide support to the bladder or bladder neck of the patient.

The first end portion 212 and the second end portion 214 are configured to be disposed within bodily tissue of the patient. In some embodiments, the first end portion 212 and the second end portion 214 are configured to be coupled to such bodily tissue to help secure the implant 205 in place within the body of the patient.

The first end portion 212 and the second end portion 214 are sized and shaped to extend between the support member 210 and the bodily tissue and coupling to the bodily tissue. For example, in one embodiment, the first end portion 212 and the second end portion 214 are configured to be disposed within and coupled to an obturator membrane of the patient, obturator muscles of the patient, or other pelvic tissue of the patient. In other embodiments, the first end portion 112 and the second end portion 114 are configured to be coupled to other bodily tissue.

In the illustrated embodiment, the first end portion 212 and the second end portion 214 include tangs 216 and 218, respectively. The tangs 216 and 218 are configured to help anchor the end portions 212 and 214 within the bodily tissue of the patient.

The implant 205 is formed with a mesh material to allow tissue in-growth to the implant 205 after implantation within the body of the patient. In some embodiments, some or all of an implant 205 can be formed with the Advantage™ Mesh or the Polyform™ Synthetic Mesh material each provided by Boston Scientific Corporation.

In the illustrated embodiment, the implant 205 is monolithically or unitarily formed. In other words, the implant 205 (including the support member 210, the first end portion 212, and the second end portion 214) are formed of a single piece of material.

The first suture 250 is coupled to the first end portion 212 of the support member 210. The first suture 250 is removably coupled to the first end portion 212. Specifically, in the illustrated embodiment, the implant 205 is formed of a mesh material and the first suture 250 forms a loop and is threaded through the first end portion 212 to slidably and removably couple the first suture 250 to the first end portion 212. The first suture 250 may be removed from the first end portion 212 of the support member 210 by severing or cutting one portion of the loop and pulling the first suture 250 in a direction away from the first end portion 212. The second suture 270 is removably coupled to the second end portion 214 in a similar manner.

The implant 205 may be placed within the body of a patient using a number of different methods. In one embodiment, implant 205 is placed within the body of the patient by making a single vaginal incision and two exit incisions. Specifically, the implant 205 is placed or implanted within the body of a patient by making an incision in an anterior wall of the vagina of the patient. End portion 212 is then coupled to an insertion tool and the end portion 212 of the implant 205 is passed through the vaginal incision to a location within the body of the patient. The insertion tool then passes through a skin incision, thereby passing the suture 250 through the skin incision. The insertion tool may then be removed from the suture 250 and removed from the body of the patient by withdrawing the tool though the vaginal incision. The insertion tool is then coupled to suture 270. The end portion 214 is passed through the vaginal incision and the end portion 214 may be placed at a location within the body of the patient (for example on an opposite side of the patient from the first end portion 212). The insertion tool may then be passed through a second skin incision, thereby passing the suture 270 through the second skin incision. The insertion tool is then decoupled from the suture 270 and is removed from the body of the patient.

The sutures 250 and 270 are then moved (for example, by pulling on the sutures in directions away from the skin incisions) to appropriately place and tension the support member 210 within the body of the patient. For example, in one embodiment, the support member 210 is placed and tensioned below a portion of the bladder of the patient.

Figure 2B:
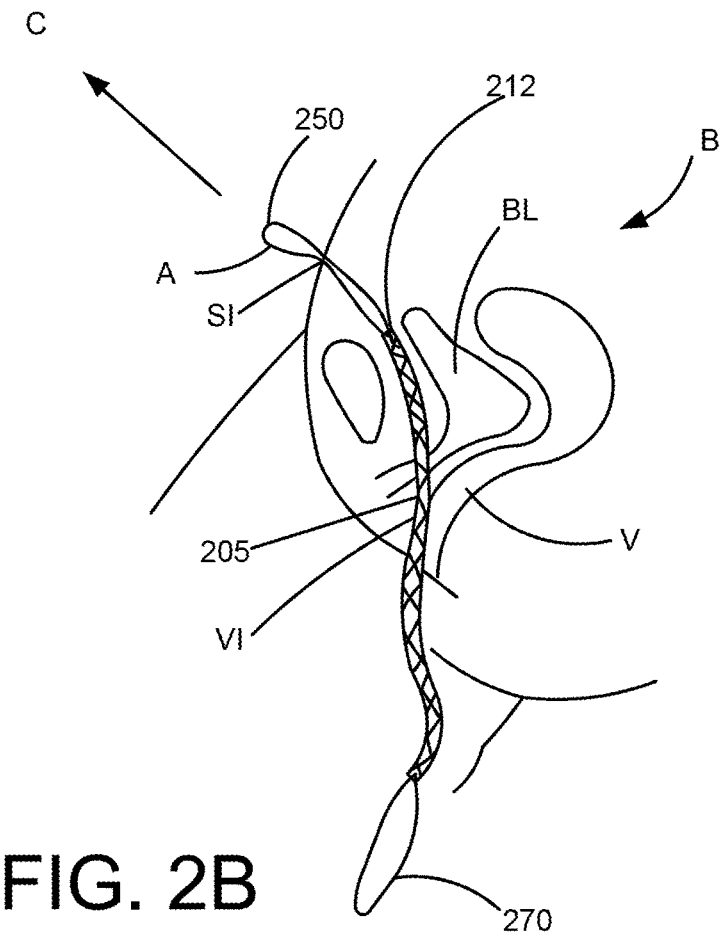
FIG. 2B is a schematic illustration of the apparatus of FIG. 2A being placed within a body of the patient.

Once the support member 210 is appropriately placed and tensioned, the sutures 250 and 270 may be removed from the end portions 212 and 214 of the implant 200. FIG. 2B schematically illustrates the implant 205 as it extends through a vaginal incision VI made in the vagina of the patient. The suture 250 extends through a skin incision SI made in a body B of a patient while the end portion 212 is disposed within the body B of the patient. The implant 205 passes along one side of the bladder BL of the patient. As illustrated in FIG. 2B with respect to suture 250, the sutures 250 and 270 may be removed from the end portions 212 and 214 by cutting a portion of the sutures 250 and 270 that is disposed outside of the body of the patient (for example, at location A in FIG. 2B) and pulling the sutures 250 and 270 in directions away from the body of the patient (for example, direction of arrow C in FIG. 2B).

Figure 2C:
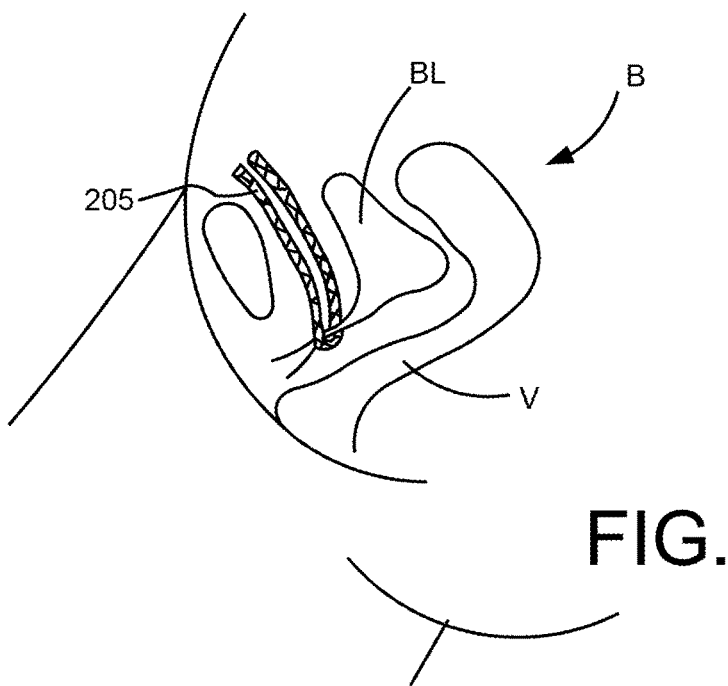
FIG. 2C is a schematic illustration of the apparatus of FIG. 2A disposed within a body of the patient.

FIG. 2C schematically illustrates the implant 205 disposed within the body of the patient such that the support member 210 is disposed between the bladder BL and the vagina V of the patient.

Figure 3:
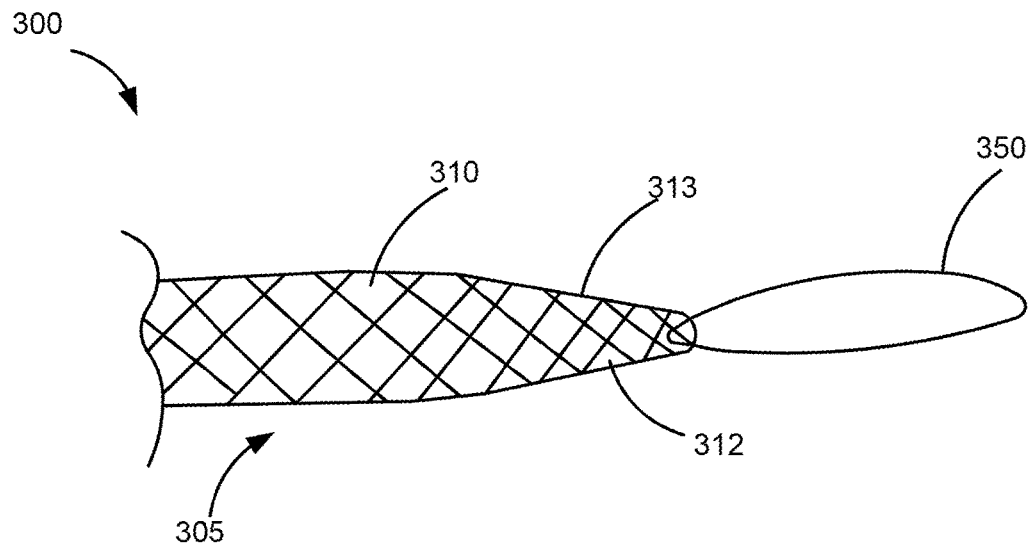
FIGS. 3 and 4 are top views of portions of apparatuses according to embodiments of the invention.

FIG. 3 is top view of a portion of an apparatus 300 according to an embodiment. The apparatus includes an implant 305 that includes a support member 310, a first end portion 312, and a second end portion (not illustrated). A suture 350 is removably coupled to the first end portion 312.

In the illustrated embodiment, the first end portion 312 includes a tapered portion 313. Specifically, the support member 310 has a width that is larger than the width than the end of the first end portion 312. In some embodiments, the tapered portion 313 is configured to assist in the delivery or placement of the implant 305. For example, in some embodiments, the tapered portion 313 dilate or help expand the tissue as the implant 305 is being placed in the body of the patient.

Figure 4:
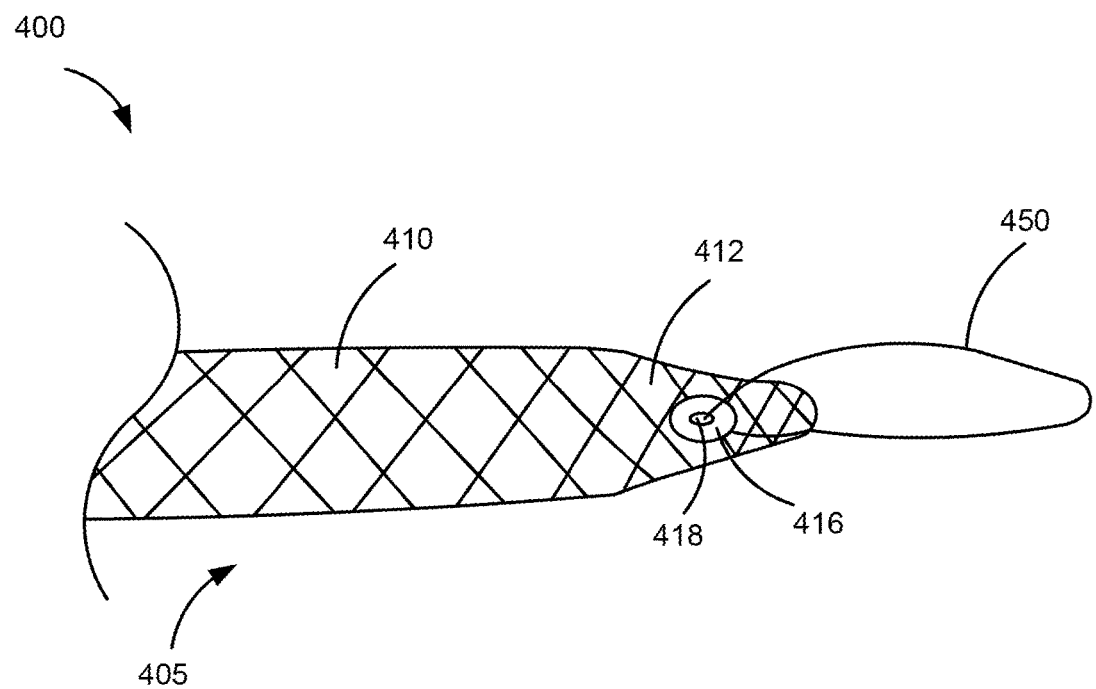

FIG. 4 is a top view of a portion of an apparatus 400 according to an embodiment. The apparatus 400 includes an implant 405 that includes a support member 410, a first end portion 412, and a second end portion (not illustrated). A suture 450 is removably coupled to the first end portion 412.

In the illustrated embodiment, the end portion 412 includes a molded portion 416. The molded portion 416 defines an opening 418. The suture 450 is threaded through the opening 418 and forms a loop to slideably and removably couple the suture 450 to the end portion 412.

The molded portion 416 is configured to provide support to the end portion 412 of the implant 400. The molded portion 416 may be formed of any type of biocompatible material and may be coupled to the implant 405 using any known methods.

Figure 5:
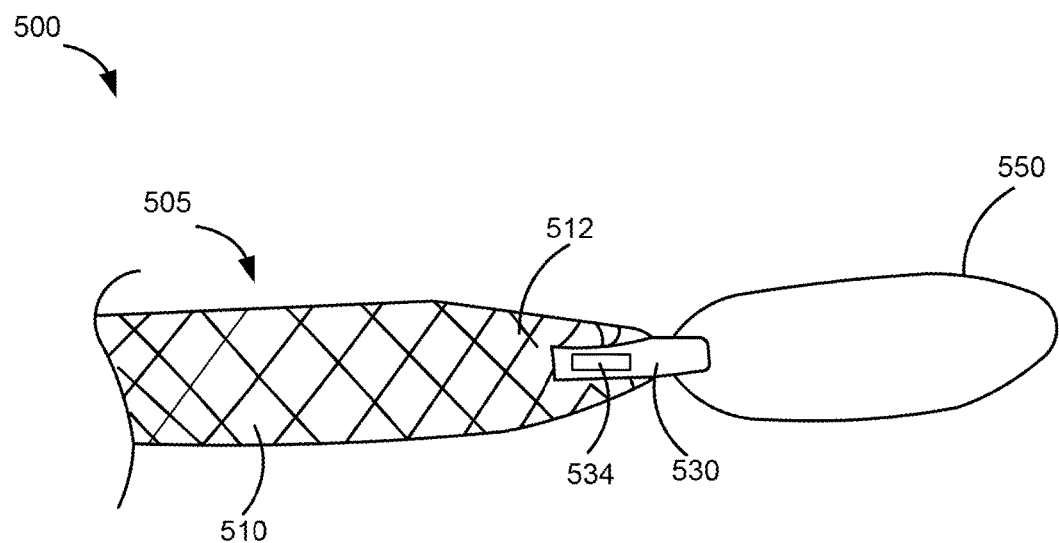
FIG. 5 is a top view of a portion of an apparatus according to an embodiment of the invention.
Figure 6:
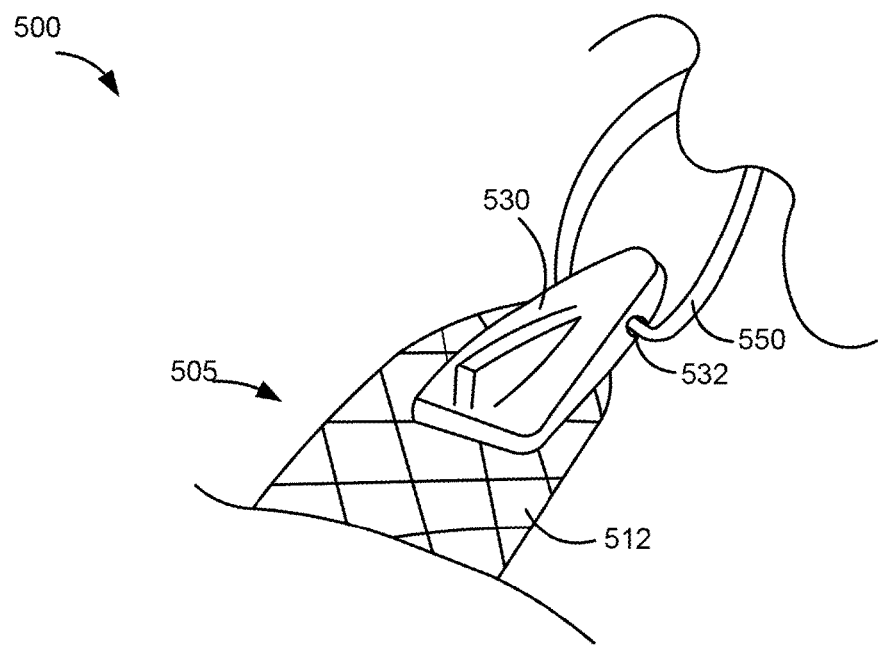
FIG. 6 is a perspective view of a portion of the apparatus of FIG. 5.

FIG. 5 is a top view of a portion of an apparatus 500 according to an embodiment. FIG. 6 is a perspective view of a portion of the apparatus 500. The apparatus 500 includes an implant 505 that includes a support member 510, a first end portion 512, and a second end portion (not illustrated). A suture 550 is coupled to the first end portion 512 of the implant 505.

The implant 505 includes a coupler 530. The coupler 530 is disposed at a distal end 513 of the end portion 512. The coupler 530 defines an opening 532 that is configured to receive the suture 550. Specifically, the suture 550 is threaded through or extends through the opening 532 and forms a loop to removably and slidably couple the suture 550 to the end portion 512 of the implant 505.

The coupler 530 also includes an anchor member 534. The anchor member 534 is configured to help anchor the implant 505 in place within the body of the patient. The anchor member 534 can be of any shape or size. For example, in some embodiments, the anchor member 534 has a barb shape. In other embodiments, the anchor member 534 has a hooked or curved shape. Although only one anchor member 534 is illustrated, the coupler 530 may include any number of anchor members.

In some embodiments, the anchor member 530 is formed of a biocompatible material and is coupled to the implant 500 using any known method. In some embodiments, the implant 505 includes tangs or tanged portions as well as an anchor member.

Figure 7:
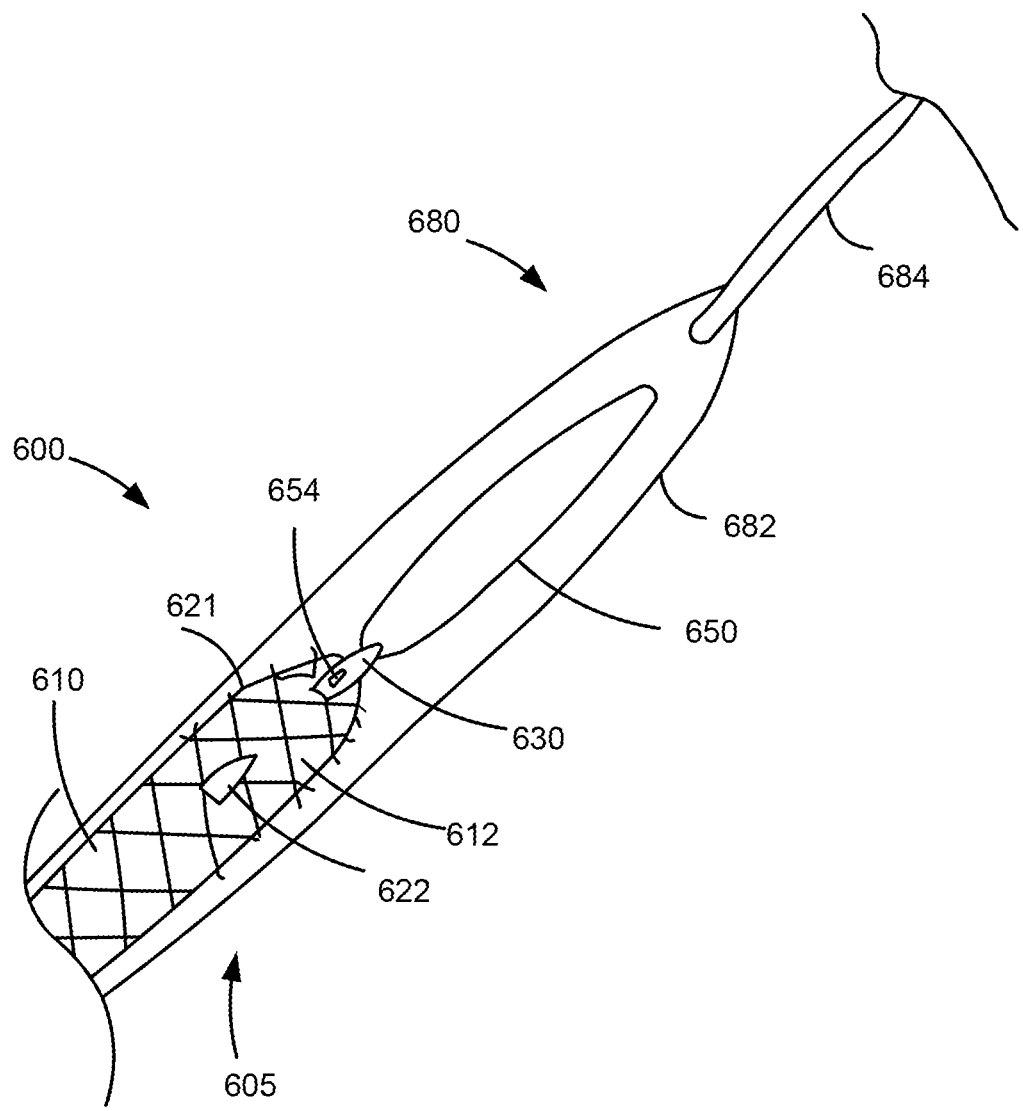
FIG. 7 is a perspective view of a portion of an apparatus according to an embodiment of the invention.

FIG. 7 is a top view of a portion of an apparatus 600 according to an embodiment. The apparatus 600 includes an implant 605 that has a support member 610, a first end portion 612, and a second end portion (not illustrated). The implant 605 also includes a coupler 630. A suture 650 is coupled to the implant 605.

The coupler 630 defines an opening (not illustrated) that is configured to receive the suture 650. Specifically, the suture 650 is coupled to the first end portion 612 of the support member 610. In the illustrated embodiment, the suture 650 forms a loop and is threaded or passed through the first end portion 612 to slidably and removably couple the suture 650 to the end portion 612 of the implant 605.

The coupler 650 includes an anchor 654 that is configured to help retain the implant 600 in place within the body of the patient. The implant 605 also includes anchor 622. Anchor 622 is also configured to help retain the implant 600 in place within the body of the patient. The coupler 650 and the anchor 622 are formed of a biocompatible material and are coupled to the implant 600 using known methods. In one embodiment, the implant 600 is formed of a mesh material and the coupler 650 and the anchor 622 are coupled to the implant 605 via an adhesive material. It should be understood that the implant 605 may include any number of anchors. In the illustrated embodiment, the implant 605 also includes a tanged portion 621.

The implant 605 is coupled to a delivery aid 680. The delivery aid 680 includes a sleeve 682 and a dilator 684. The sleeve 682 is coupled to the implant 605 and defines a lumen. The lumen is configured to receive at least a portion of the first end portion 612 and the suture 650. In the illustrated embodiment, the entire suture 650 is disposed within the lumen defined by the sleeve 682. Although only one delivery aid is illustrated and discussed in detail, it should be understood that the implant 605 may be coupled to any number of delivery aids (such as a second delivery aid coupled to the second end portion of the implant).

In some embodiments, the sleeve 682 is configured to allow the implant 605 to be smoothly placed within the body of the patient. Specifically, in the illustrated embodiment, the tanged portion 621 of the implant 605, the anchor 622, and the anchor 654 are disposed within the lumen defined by the sleeve 682. Accordingly, the tanged portion 621, the anchor 622, and the anchor 654 do not engage bodily tissue as the implant 605 is inserted into the body of the patient.

The dilator 684 is coupled to a distal end portion 683 of the sleeve 682. The dilator 684 is configured to dilate bodily tissue as the implant is placed within the body of the patient. The dilator 684 is configured to be removably coupled to an insertion tool for placement within the body of the patient.

The implant 605 may be placed within the body of the patient using any number of methods, including inside-out methods (passing the implant and the insertion tool from a vaginal incision to an outer skin incision) and outside-in methods (passing the insertion tool from a skin incision to a vaginal incision prior to coupling the implant to the insertion tool).

In one embodiment, the implant 605 is inserted into the patient such that the dilator 684 and the sleeve 682 extend from a skin incision and the first end portion 612 is disposed within the body of the patient. The sleeve 682 and the dilator 684 are removed from the implant 605. In one embodiment, the sleeve 682 may be cut (for example at a location proximal the vaginal incision) to remove the sleeve from the implant 605. The dilator 684 and sleeve 682 may then be pulled in a direction way from the implant 605 to remove delivery aid 680 from the implant 605. Once the sleeve 682 is removed, the tanged portion 621, the anchor 622, and the anchor 654 may engage bodily tissue to help retain and secure the implant 605 in place within the body of the patient.

In one embodiment, a single sleeve extends from the first end portion 612 of the implant 605 to the second end portion of the implant 605.

In one embodiment, prior to removing the delivery aid 680 from the implant, the delivery aid 680 may be used to position and tension the implant within the body. The delivery aid 680 may then be removed. The sutures 650 may then be used to further tension the implant 605. For example, the sutures 650 may be used to further tension the implant 605 a few days (for example, 24 hours or 48 hours) after the procedure to place the implant within the body of the patient.

As described above, the suture 650 may be removed from the implant 605 by cutting a portion of the suture 650 and pulling the suture in a direction away from the implant 605.

In one embodiment, an apparatus includes a support member configured to provide support to a portion of a body of a patient. The support member has a first end portion and a second end portion. The first end portion of the support member is configured to be disposed within a body of a patient. The apparatus also includes a suture removably coupled to the first end portion of the support member. The suture is configured to extend through an incision in the body of the patient from a location within the body of the patient to a location outside of the body of the patient.

In one embodiment the suture includes a looped portion and is threaded through the first end portion of the support member. In another embodiment, the suture is formed from a non-resorbable material.

In one embodiment, the suture is a first suture and the incision is a first incision, the apparatus includes a second suture coupled to the second end portion of the support member. The second suture is configured to extend through a second incision in the body of the patient from a location within the body of the patient to a location outside of the body of the patient. The second incision is different than the first incision.

In one embodiment, the first end portion of the support member defines an opening and the suture extends through the opening defined by the first end portion. In one embodiment, the apparatus includes a coupling member coupled to the first end portion and defining an opening. The suture includes a loop portion extending through the opening defined by the coupling member. In one embodiment, the apparatus includes a coupling member coupled to the first end portion and defining an opening. The coupling member includes a barb member configured to help secure the implant within the body of the patient. The suture includes a loop portion extending through the opening defined by the coupling member.

In one embodiment, the apparatus includes a barb member configured to help secure the implant within the body of the patient. In one embodiment, the first end portion includes a tapered portion. In one embodiment, the apparatus includes a sleeve member. The sleeve member defines a lumen. The end portion of the support member and the suture are disposed within the lumen defined by the sleeve member.

In one embodiment, the apparatus includes a sleeve member. The sleeve member defines a lumen. The end portion of the support member and the suture are disposed within the lumen defined by the sleeve member. The apparatus also includes a dilator coupled to the sleeve member.

In one embodiment a method of placing an implant within a body of a patient includes (a) inserting the implant into the body of the patient, the implant includes a support member having a first end portion and a second end portion, a suture is removably coupled to the first end portion of the support member, (b) positioning the implant within the body of the patient such that the first end portion is disposed within the body of the patient and the suture extends from a location within the body of the patient to a location outside of the body of the patient, and (c) removing the suture from the first end portion such that no portion of the suture remains within the body of the patient.

In one embodiment, the inserting includes inserting the implant into the body of the patient through a first incision in the body of the patient and the positioning includes passing the suture through a second incision in the body the patient, the second incision being different than the first incision. In another embodiment, the suture includes a loop and extends through the first end portion and the removing includes cutting a portion of the loop and pulling the suture through the first end portion.

In one embodiment, the method includes adjusting the location of the implant within the body of the patient by pulling the suture to cause more of the suture to be disposed outside of the body of the patient.

In one embodiment, the suture is a first suture and a second suture is removably coupled to the second end portion. The method further includes positioning the implant within the body of the patient such that the second end portion is disposed within the body of the patient and the second suture extends from a location within the body of the patient to a location outside of the body of the patient.

In one embodiment, the suture is a first suture and a second suture is removably coupled to the second end portion. The inserting includes inserting the implant into the body of the patient through a first incision in the body of the patient and the positioning includes passing the suture through a second incision in the body the patient, the second incision being different than the first incision. The method also includes passing the second suture through a third incision in the body of the patient, the third incision being different than the first incision and the second incision.

In one embodiment, a method of placing an implant within a body of a patient includes (a) inserting the implant into the body of the patient, the implant includes a support member having a first end portion and a second end portion, a suture removably coupled to the first end portion of the support member, and a sleeve coupled to the first end portion of the support member and defining a lumen, the suture and the first end portion being disposed within the lumen defined by the sleeve, (b) positioning the implant within the body of the patient such that the first end portion is disposed within the body of the patient and the suture extends from a location within the body of the patient to a location outside of the body of the patient, and (c) removing the sleeve from the first end portion of the support member such that the suture remains coupled to the first end portion of the support member and extends from a location within the body of the patient to a location outside of the body of the patient.

In one embodiment, the method includes, after the removing, cutting a portion of the suture and removing the suture from the first end portion of the support member. In another embodiment, the method includes, after the removing, adjusting the location of the implant within the body of the patient by pulling the suture.

While certain features of the described implementations have been illustrated as described herein, many modifications, substitutions, changes and equivalents will now occur to those skilled in the art. For example, although the procedures above have focused on placing a device within a female patient, the apparatuses and methods disclosed herein may be used on male patients. It is, therefore, to be understood that the appended claims are intended to cover all such modifications and changes as fall within the scope of the embodiments.

What is claimed is:

1. An apparatus, comprising:
   a support member configured to provide support to a portion of a body of a patient;
   the support member having a first end portion and a second end portion, the first end portion of the support member being configured to be disposed within a body of a patient, the first end portion including a tapered portion;
   a suture including a loop portion;
   a dilator;
   a sleeve member having a proximal end portion and a distal end portion, the dilator coupled to the distal end portion of the sleeve member, the sleeve member defining a lumen, the first end portion of the support member and the entire suture being disposed within the lumen defined by the sleeve member; and
   a coupling member coupled to the first end portion and defining an opening, the loop portion of the suture configured to extend through the opening defined by the coupling member.

2. The apparatus of claim 1, wherein the suture is formed from a non-resorbable material.

3. The apparatus of claim 1, wherein the suture is a first suture, further comprising:
   a second suture coupled to the second end portion of the support member.

4. The apparatus of claim 1, further comprising:
   wherein the coupling member includes a barb member configured to help secure the support member within the body of the patient.

5. The apparatus of claim 1, further comprising:
   a barb member configured to help secure the support member within the body of the patient.

6. The apparatus of claim 1, wherein the first end portion of the support member includes a tanged portion,
   wherein the coupling member includes a barb member configured to help secure the support member within the body of the patient, the apparatus further comprising:
   an anchor member coupled to a surface of the first end portion of the support member,
   wherein the tanged portion, the barb member, and the anchor member are disposed entirely within the lumen of the sleeve member.

7. The apparatus of claim 6, wherein the anchor member is coupled to the surface of the first end portion using an adhesive.

8. The apparatus of claim 1, wherein the support member includes a tanged portion.

9. An apparatus, comprising:
   a support member configured to provide support to a portion of a body of a patient;
   the support member having a first end portion and a second end portion, the first end portion of the support member being configured to be disposed within a body of a patient, the first end portion including a tapered portion;
   a suture;
   a coupling member coupled to the tapered portion of the first end portion, the coupling member defining an opening, the suture including a loop portion extending through the opening defined by the coupling member;
   a dilator; and
   a sleeve member having a proximal end portion and a distal end portion, the dilator coupled to the distal end portion of the sleeve member, the sleeve member defining a lumen, the first end portion of the support member, the coupling member, and the entire suture being disposed within the lumen defined by the sleeve member.

10. The apparatus of claim 9, wherein no portion of the suture is fixedly coupled to the coupling member.

11. The apparatus of claim 9, wherein the first end portion of the support member defines a longitudinal axis, the opening extending in a direction perpendicular to the longitudinal axis.

12. The apparatus of claim 9, wherein the coupling member includes a first anchor member, the first end portion of the support member includes tangs, and the first end portion of the support member includes a second anchor, wherein the first anchor, the tangs, and the second anchor are entirely disposed within the lumen defined by the sleeve member.

* * * * *